US009802973B2

(12) United States Patent
Childs

(10) Patent No.: US 9,802,973 B2
(45) Date of Patent: Oct. 31, 2017

(54) CRYSTALLINE FORMS OF FERRIC MALTOL

(71) Applicant: SHIELD TX (UK) LTD., Gateshead Quays (GB)

(72) Inventor: David Paul Childs, Gateshead Quays (GB)

(73) Assignee: SHIELD TX (UK) LTD., Gateshead Quays (GB)

( * ) Notice: Subject to any disclaimer, the term of this patent is extended or adjusted under 35 U.S.C. 154(b) by 0 days.

(21) Appl. No.: 15/039,943

(22) PCT Filed: Oct. 23, 2015

(86) PCT No.: PCT/EP2015/074653
§ 371 (c)(1),
(2) Date: May 27, 2016

(87) PCT Pub. No.: WO2016/066555
PCT Pub. Date: May 6, 2016

(65) Prior Publication Data
US 2017/0260222 A1   Sep. 14, 2017

(30) Foreign Application Priority Data
Oct. 28, 2014   (GB) .................................. 1419174.6

(51) Int. Cl.
*C07F 15/02*   (2006.01)

(52) U.S. Cl.
CPC ........ *C07F 15/025* (2013.01); *C07B 2200/13* (2013.01)

(58) Field of Classification Search
CPC ............................ C07F 14/025; C07B 2200/13
See application file for complete search history.

(56) References Cited

U.S. PATENT DOCUMENTS

| 4,575,502 A | 3/1986 | Hider et al. |
| 7,459,569 B2 | 12/2008 | Stockham |

FOREIGN PATENT DOCUMENTS

| EP | 0 159 917 | 10/1985 |
| GB | 2531742 | 10/1916 |
| WO | WO 03/097627 | 11/2003 |
| WO | WO 2012/101442 | 8/2012 |

OTHER PUBLICATIONS

Notification of Grant issued in United Kingdom Application No. 1419174.6, dated Sep. 6, 2016.
Office Communication issued in Australian Application No. 2015340825, dated Sep. 28, 2016.
Written Opinion of the International Preliminary Examining Authority issued in International Application No. PCT/EP2015/074653, dated Oct. 14, 2016.
International Preliminary Report on Patentability issued in International Application No. PCT/EP2015/074653, dated Jan. 18, 2017.
Office Communication issued in Canadian Application No. 2,944,210, dated Dec. 8, 2016.
Gasche et al, "Ferric maltol is effective in correcting iron deficiency anemia in patients with inflammatory bowel disease: results from a phase-3 clinical trial program", *Inflamm Bowel Dis*,21(3): 579-588, 2015.
International Search Report and Written Opinion issued in International Application No. PCT/EP2015/074653, dated Jan. 5, 2015.
Office Communication issued in United Kingdom Application No. 1419174.6, dated Jun. 2, 2016.
Schlindwein et al, "New lipophilic 3-hydroxy-4-pyridinonate iron(III) complexes: synthesis and EXAFS structural characterisation", *Dalton Transactions*, 10: 1313-1321, 2006.
Search Report issued in United Kingdom Application No. 1419174.6, dated Aug. 4, 2015.
Zborowski et al.,"Vibrational and computational study on maltol (3-hydroxy-2-methyl-4h-pyran-4-one) polymorphism", *Vibrational Spectroscopy*, 37: 233-236, 2005.

*Primary Examiner* — Timothy R Rozof
(74) *Attorney, Agent, or Firm* — Parker Highlander PLLC

(57) ABSTRACT

There is provided polymorphs of ferric maltol. Such forms may be useful in the treatment of iron deficiency with or without anaemia, such as iron deficiency anaemia.

28 Claims, 9 Drawing Sheets

Flow diagram of General Polymorph Manufacture
Molecular Formula: $(C_6H_5O_3)_3Fe$

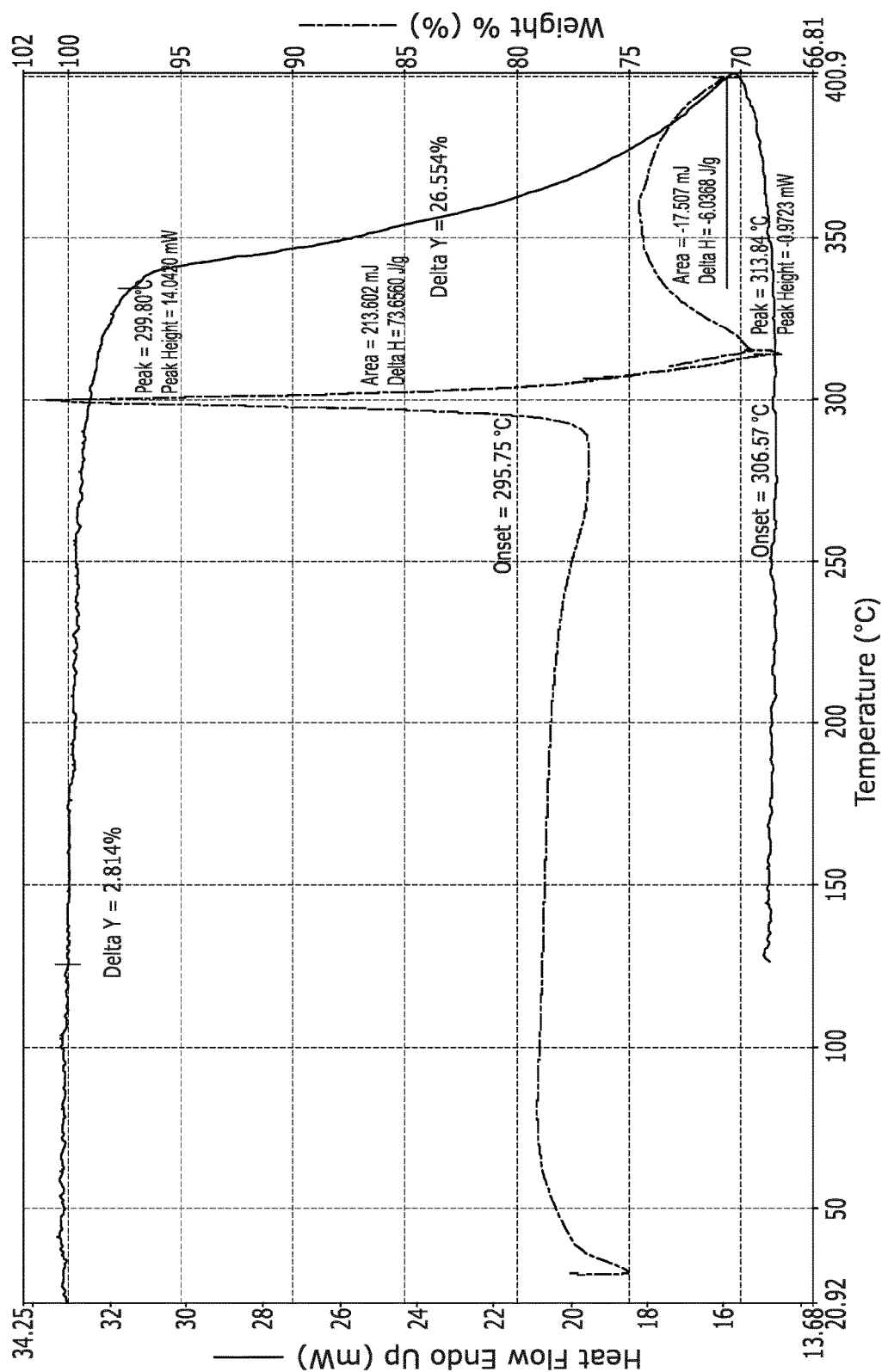
Figure 2: TGA and DSC of Form I

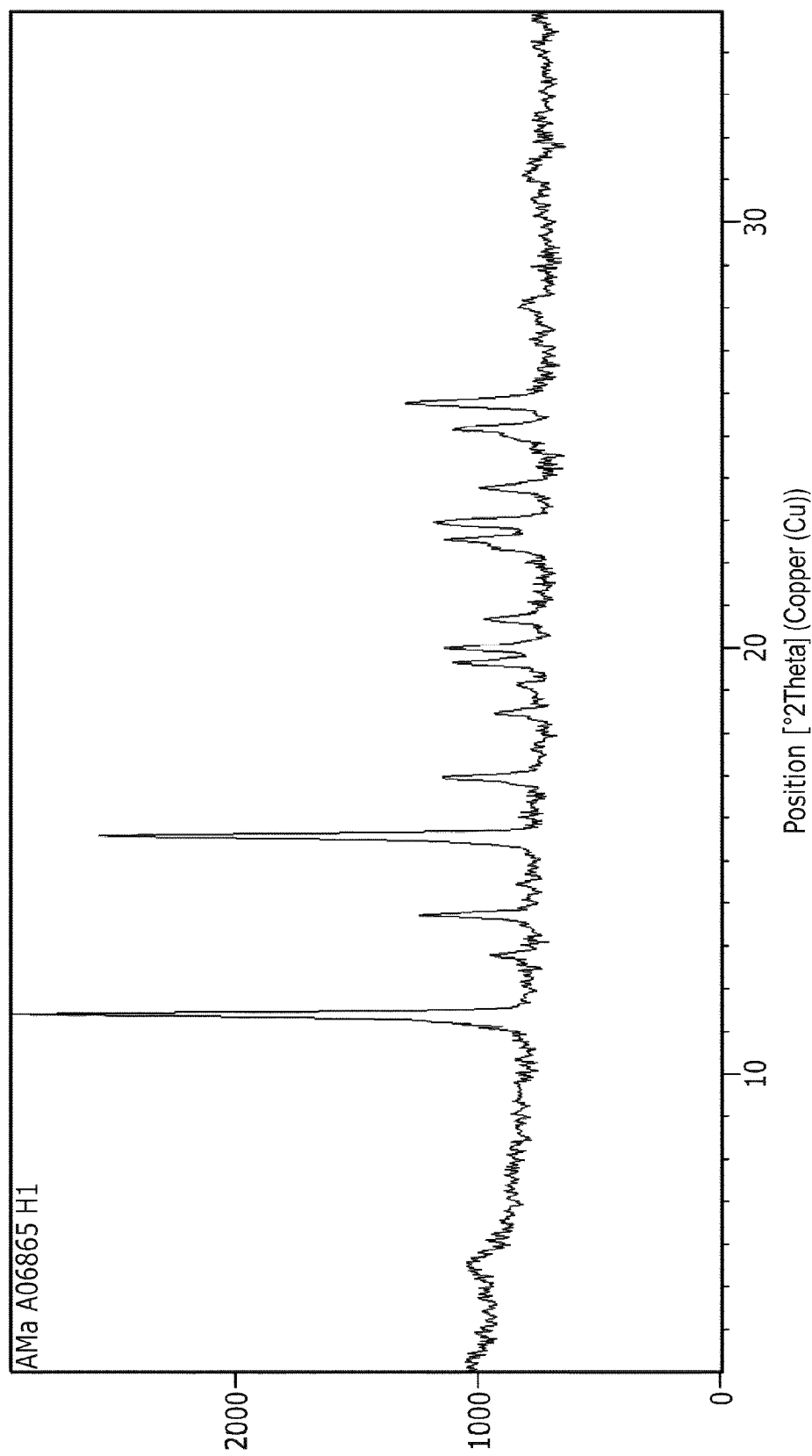
Figure 3: XRPD of Form I

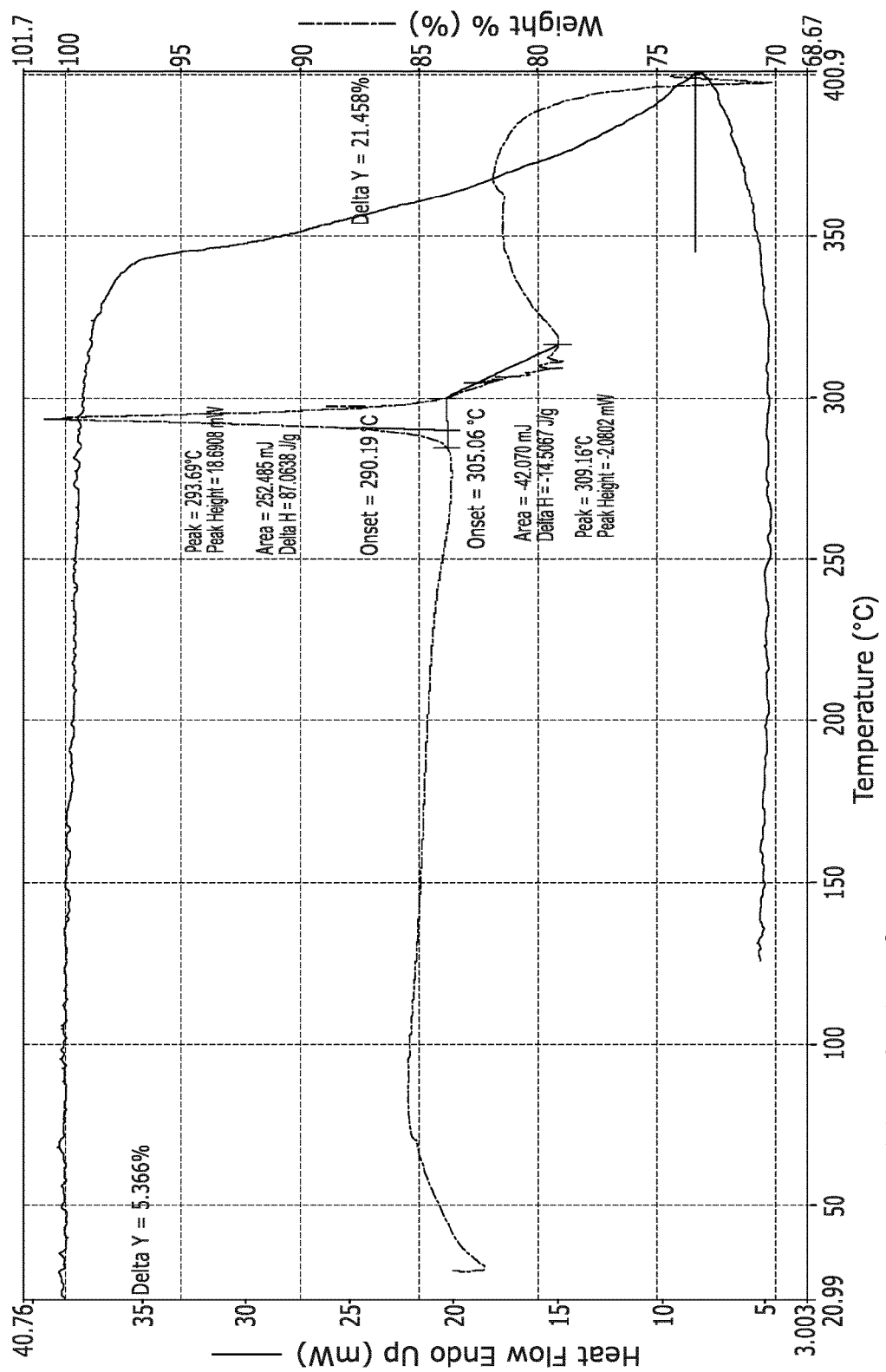
Figure 4: DSC and TGA of Form II

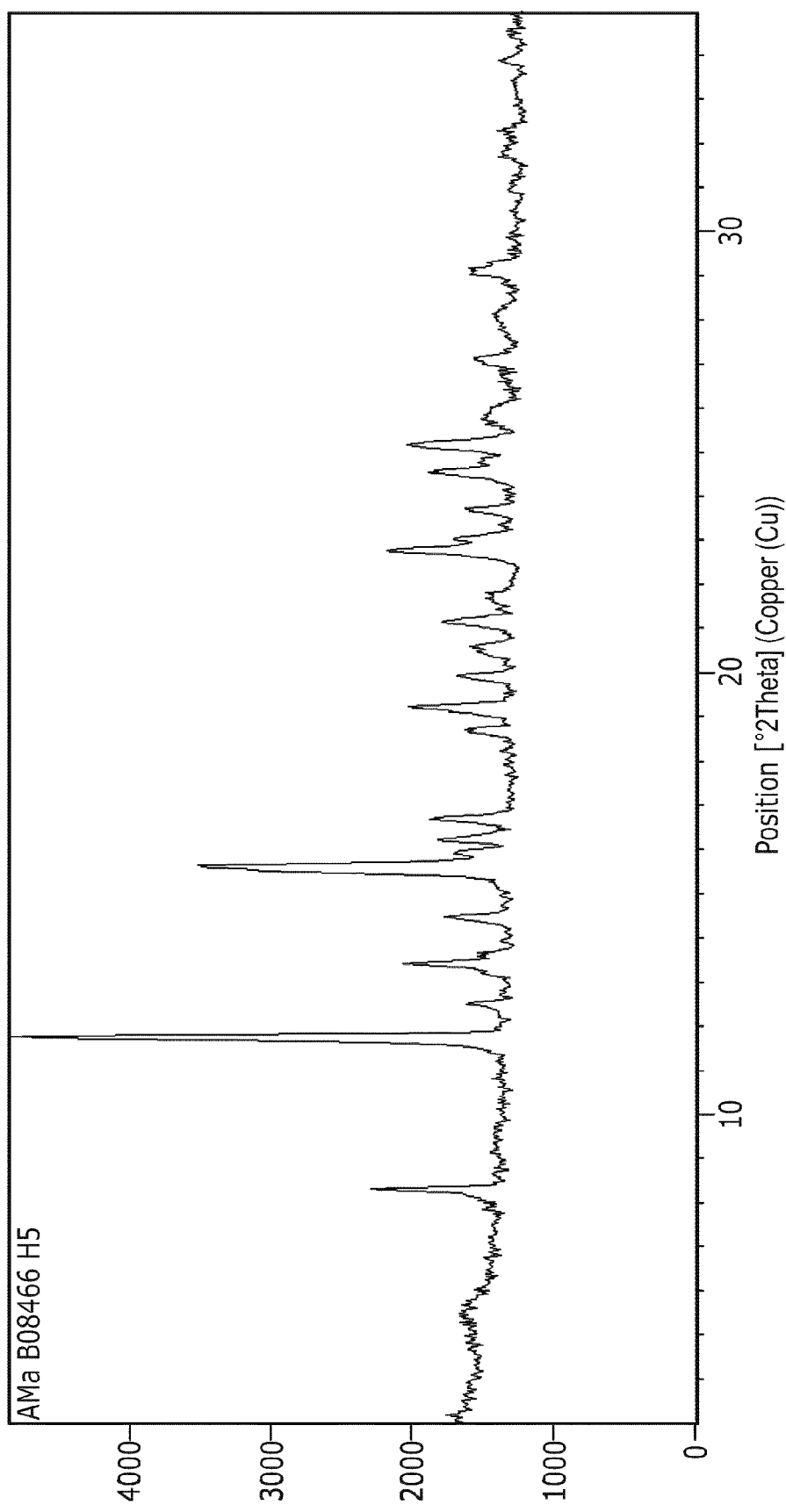
Figure 5: XRPD of Form II

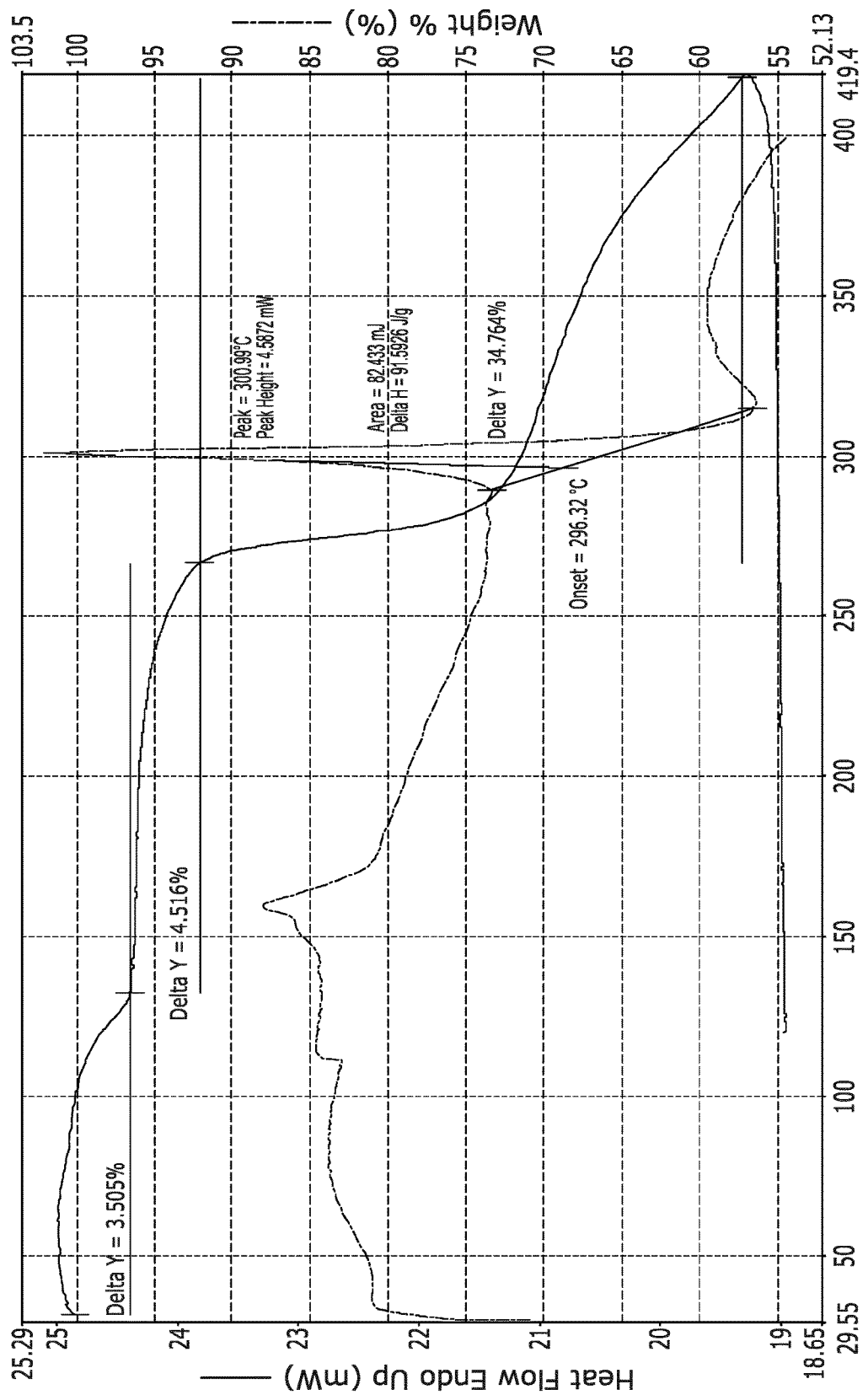
Figure 6: DSC and TGA of Form III

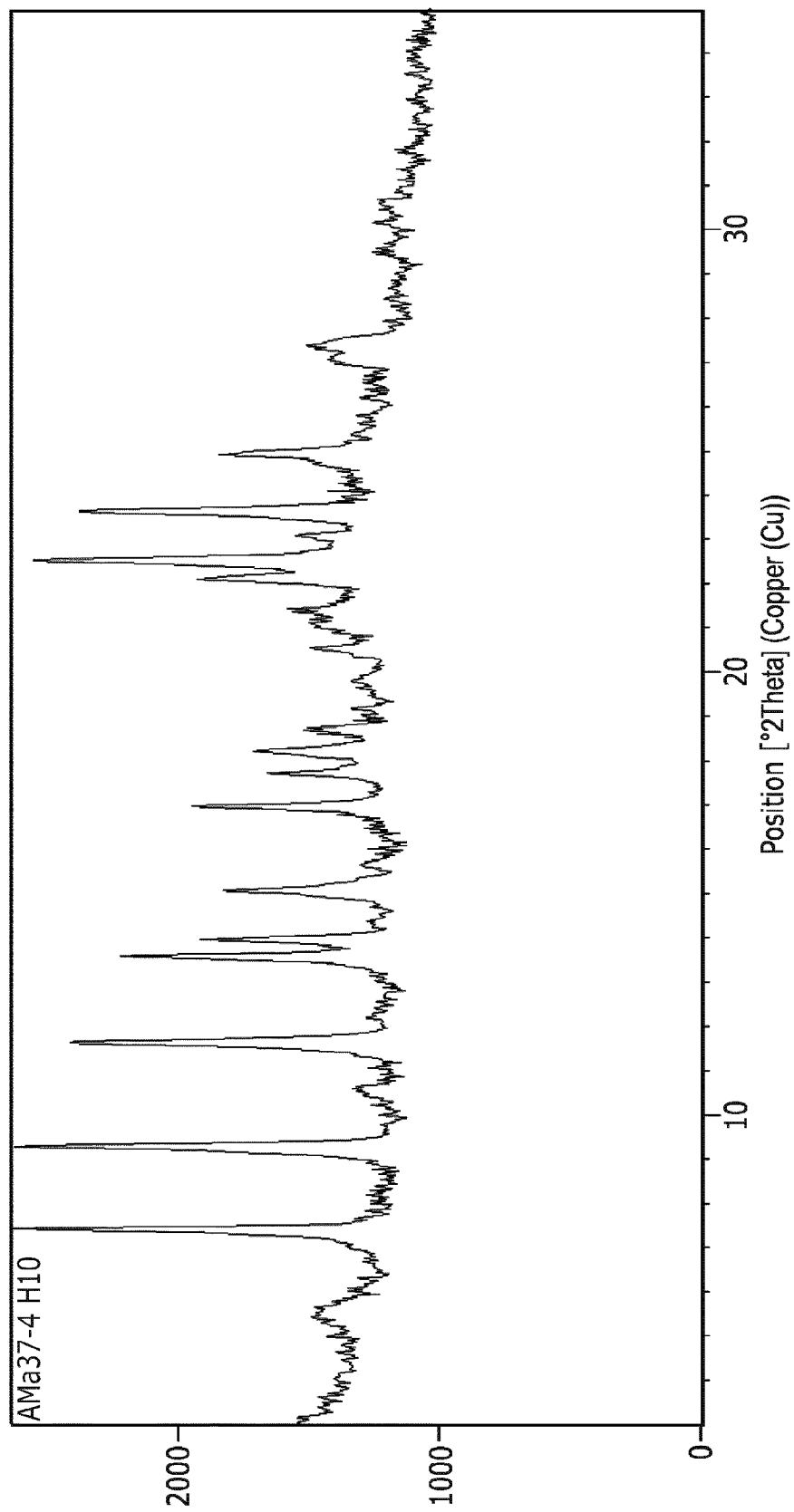

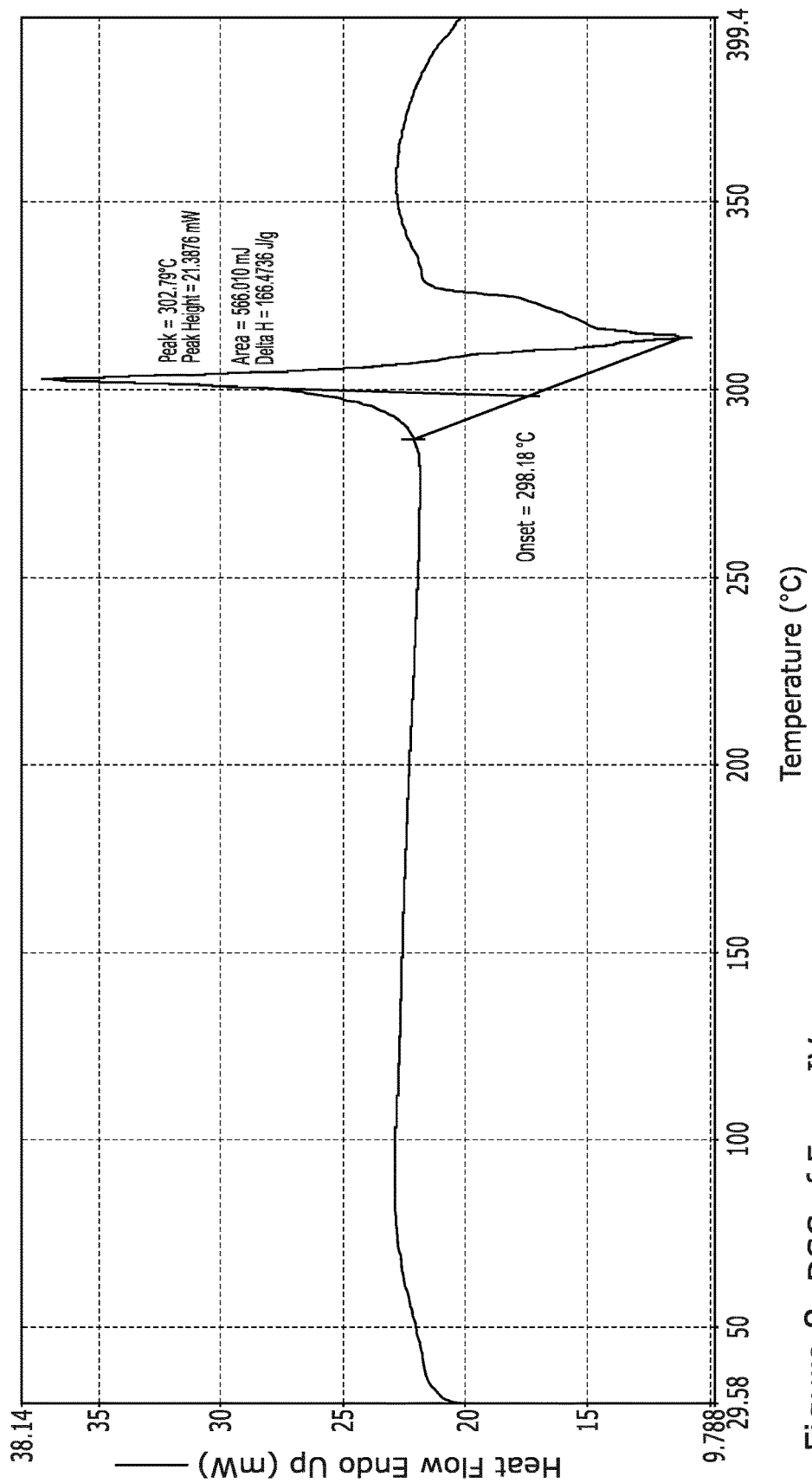
Figure 8: DSC of Form IV

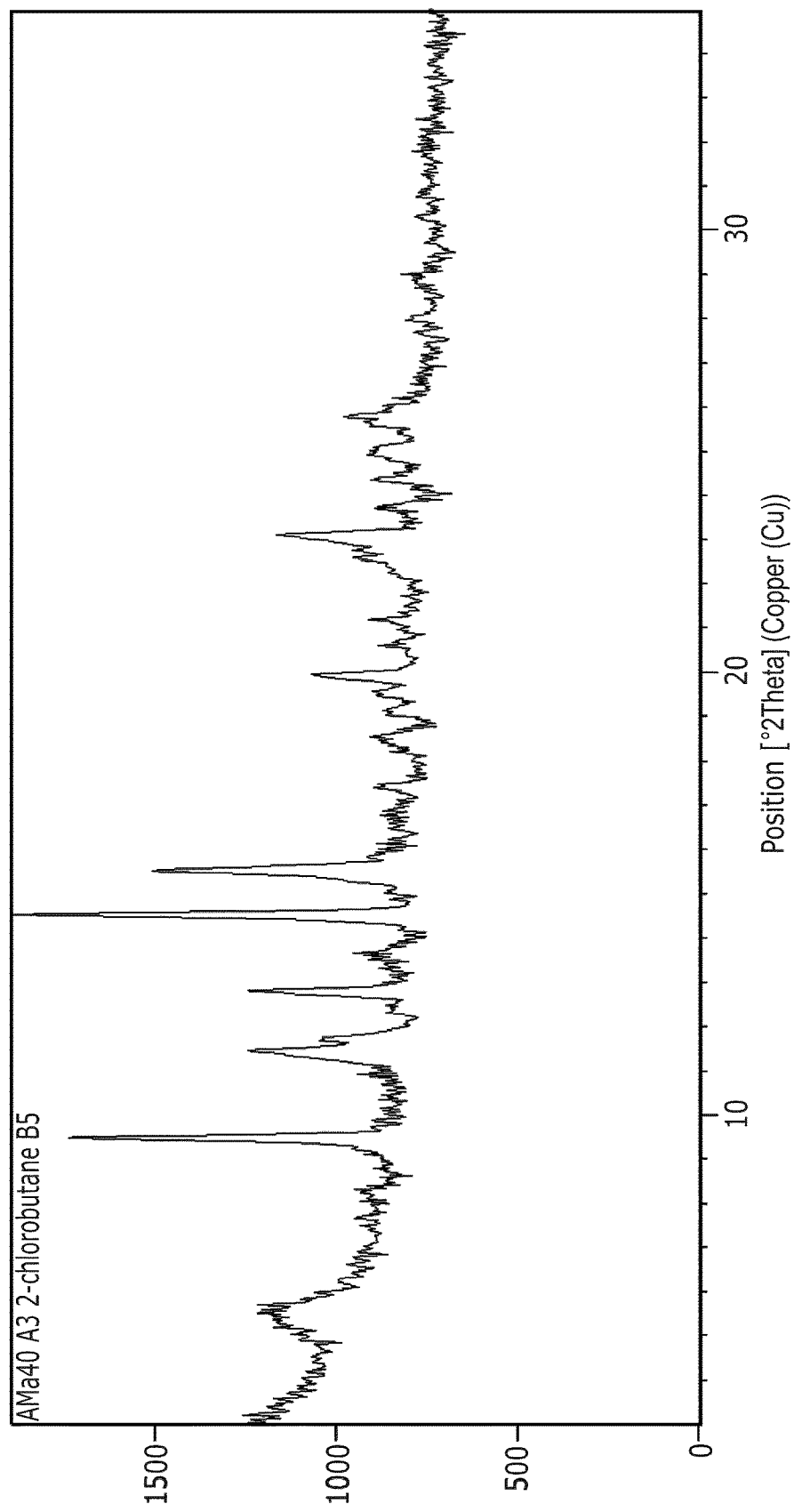
Figure 9: XRPD of Form IV

CRYSTALLINE FORMS OF FERRIC MALTOL

This application is a national phase application under 35 U.S.C. §371 of International Application No. PCT/EP2015/074653, filed Oct. 23, 2015, which claims priority to United Kingdom Application No. 1419174.6, filed Oct. 28, 2014. The entire text of each of the above referenced disclosures is specifically incorporated herein by reference.

This invention relates to new polymorphs of a compound, to pharmaceutical compositions containing them, and to processes for obtaining them.

An adequate supply of iron to the body is an essential requirement for tissue growth and the maintenance of good health in both man and animals. Moreover, in certain pathological conditions where there is an insidious blood loss, or where there is a mal-distribution of iron in the body, there may be a state of low iron stores in the body leading to an iron deficiency and a concomitant chronic anaemia. This is seen in inflammatory diseases of the gastrointestinal tract, such as gastric and peptic ulcers, reflux oesophagitis, ulcerative colitis and Crohn's disease.

Anaemia can also follow operations that result in serious blood loss and can be associated with gastrointestinal infections, such as those caused by *Helicobacter pylori*.

Ferric maltol comprises a complex of one ferric iron and three maltol anions and has the following molecular formula: $(C_6H_5O_3)_3Fe$. Maltol is also known as 3-hydroxy-2-methyl-4-pyrone.

Polymorphic forms occur where the same composition of matter crystallises in a different lattice arrangement, resulting in different thermodynamic properties and stabilities specific to the particular polymorphic form.

WO 03/097627 A1 discloses a method of forming iron hydroxypyrone compounds.

EP 0 159 917 A3 describes a pharmaceutical composition containing a hydroxypyrone-iron complex.

WO 2012/101442 A1 discloses a method of forming iron hydroxypyrone compounds.

Schlindwein et al (Dalton Transactions, 2006, Vol. 10, pages 1313-1321) describes lipophilic 3-hydroxy-4-pyridinonate iron(III) complexes.

Ferric maltol has been known for about 100 years but no polymorphs have been identified or studied prior to this invention.

We have now found that it is possible to produce different polymorphs of ferric maltol, which crystalline forms may be referred to herein as the "compounds of the invention". One polymorph form can be preferable in some circumstances when certain aspects, such as ease of preparation and stability, such as thermodynamic stability are required. In other situations, a different polymorph may be preferred for greater solubility and/or superior pharmacokinetics. The polymorphs of the invention can provide advantages in terms of improved or better bioavailability or improved or better stability or solubility.

The term "ferric maltol" as used herein refers to both ferric trimaltol and the designation INN ferric maltol.

In one aspect of the invention there is provided a Form I polymorph of ferric maltol characterized by a powder X-ray diffraction pattern comprising characteristic crystalline peaks expressed in degrees 2-theta at each of 15.6 and 22.5±0.25 or 0.2 degrees, optionally wherein the Form I polymorph comprises greater than about 92 wt. % ferric maltol based on the weight of the polymorph, such as greater than about 95 wt. %, preferably greater than about 96 wt. %, or about 98 wt. %, or about 99 wt. % such as about 99.8 wt. %.

In a further aspect of the invention there is provided a Form II polymorph of ferric maltol characterized by a powder X-ray diffraction pattern comprising a peak expressed in degrees 2-theta at 8.3±0.25 degrees.

In a yet further aspect of the invention there is provided a Form III polymorph of ferric maltol characterized by a powder X-ray diffraction pattern comprising a peak expressed in degrees 2-theta at 7.4±0.25 degrees.

In a still further aspect of the invention there is provided a Form IV polymorph of ferric maltol characterized by a powder X-ray diffraction pattern comprising peaks expressed in degrees 2-theta at 9.5 and 14.5±0.2 degrees.

The measurements of degrees 2-theta generally refer to measurements at ambient temperature, such as from about 5 to about 40° C., preferably about 10 to about 30° C.

The relative intensities of the peaks can vary, depending on the sample preparation technique, the sample mounting procedure, the particular instrument employed, and the morphology of the sample. Moreover, instrument variation and other factors can affect the 2-theta values. Therefore, XRPD peak assignments for the polymorphs of the invention, as defined herein in any embodiment, can vary by, for example, ±0.2, such as ±0.1 or ±0.05. The term "about" in relation to XRPD peak values may include for example, ±0.25 or ±0.2, such as ±0.1 or ±0.05. These ranges may apply to any of the peak values in degrees referred to herein.

In another embodiment of the invention, there is provided a process for the preparation of a ferric maltol polymorph, such as Form I or Form II polymorph, which comprises combining ferric citrate with maltol anions to form a mixture comprising ferric maltol and wherein the process comprises the use of a ferric maltol seed crystal. The seed crystal may comprise a Form I and/or Form II polymorph as described herein and these polymorphs may be prepared using the methods described herein.

In another aspect of the invention, there is provided a process for the preparation of Form I polymorph, which comprises combining ferric citrate with maltol anions to form a mixture comprising ferric maltol polymorph Form I wherein the process comprises the use of a ferric maltol seed crystal comprising Form I and/or Form II polymorph and preferably wherein the polymorph formed is washed (typically with water) prior to drying.

In a further aspect of the invention, there is provided a process for the preparation of Form II polymorph, which comprises combining ferric citrate with maltol anions in solution to form a mixture comprising ferric maltol polymorph Form II, wherein the process preferably comprises the use of a ferric maltol seed crystal comprising Form I and/or Form II polymorph and preferably wherein the polymorph formed is washed (typically with water) prior to drying.

The invention also provides a pharmaceutical composition comprising a polymorph according to the invention, or mixtures thereof, and a pharmaceutically acceptable adjuvant, diluent or carrier.

In addition, the invention provides a composition comprising Form I and Form II polymorphs as defined herein.

In an aspect of the invention, the polymorph of the invention is for use in the prevention or treatment of iron deficiency with or without anaemia in a subject. The anaemia is preferably iron deficiency anaemia.

In a further aspect of the invention there is provided the use of a polymorph of the invention for the manufacture of a medicament for the prevention or treatment of iron deficiency with or without anaemia in a subject. The anaemia is preferably iron deficiency anaemia.

The invention further provides a method for the prevention or treatment of iron deficiency with or without anaemia which method comprises the administration of a polymorph according to the invention to a subject in need of such treatment. The anaemia is preferably iron deficiency anaemia.

Preferably the polymorphs of the invention are obtained in forms that are greater than about 90%, such as greater than about 95%, crystalline (e.g. greater than about 98% crystalline and, particularly, 100%, or nearly 100%, crystalline). By "substantially crystalline" we include greater than about 60%, preferably greater than about 75%, and more preferably greater than about 80% (such as about 90%) crystalline. The degree (%) of crystallinity may be determined by the skilled person using X-ray powder diffraction (XRPD). Other techniques, such as solid state NMR, FT-IR, Raman spectroscopy, differential scanning calorimetry (DSC) microcalorimetry and calculations of the true density may also be used.

The polymorphs of the invention may be characterised by an X-ray powder diffraction pattern comprising the following characteristic crystalline peaks with approximate 2-Theta values (in degrees) as well as an indication of the relative intensity of those peaks in brackets, where a percentage relative intensity of approximately 25-100% is termed "vs" (very strong), approximately 10-25% is termed "s" (strong), approximately 3-10% is termed "m" (medium) and approximately 1-3% is termed "w" (weak).

Form I:

The Form I polymorph preferably comprises characteristic crystalline peaks with 2-Theta values (in degrees) of around (i.e. at about or at approximately) 15.6 and 22.5±0.25, or 0.2 degrees. The diffraction pattern typically does not comprise peaks at one or more, or all, or each of, about 6.9, 7.4, 8.3, 9.3, 10.5, or about 11.8 degrees, such as 8.3 or 11.8±0.25, or ±0.2, or ±0.1 such as about ±0.05 degrees.

Preferably, the Form I polymorph of ferric maltol is characterized by a powder X-ray diffraction pattern comprising characteristic crystalline peaks expressed in degrees 2-theta at 15.6 and 22.5±0.2 or ±0.1 such as about ±0.05 degrees.

The Form I polymorph may be characterised by a powder X-ray diffraction pattern comprising one or more further peaks expressed in degrees 2-theta selected from about 11.4, 12.8, 13.7, 16.9, 18.5, 19.6, 20.0, 20.7, 23.0, 23.8, 25.2, 25.8, or 28.0±0.25 or ±0.2, or ±0.1 such as about ±0.05 degrees.

Preferably, the Form I polymorph is characterised by a powder X-ray diffraction pattern comprising two or more, three or more, four or more, or five or more further peaks expressed in degrees 2-theta selected from about 11.4, 12.8, 13.7, 16.9, 18.5, 19.6, 20.0, 20.7, 23.0, 23.8, 25.2, 25.8, or 28.0±0.25 or ±0.2, or ±0.1 such as about ±0.05 degrees.

For example, the Form I polymorph preferably comprises characteristic crystalline peaks with 2-Theta values (in degrees) at each of 11.4, 15.6, 16.9, 22.5, and 23.8, and, optionally, one or more, two or more, three or more, or each of, 13.7, 19.6, 20.7, 22.5, 25.2 and 25.8±0.2, or ±0.1 such as about ±0.05 degrees.

For example, the Form I polymorph may be characterised by a powder X-ray diffraction pattern comprising peaks expressed in degrees 2-theta at each of about 11.4, 12.8, 13.7, 15.6, 16.9, 18.5, 19.6, 20.0, 20.7, 22.5, 23.0, 23.8, 25.2 and 25.8±0.2 or ±0.1 such as about ±0.05 degrees, optionally wherein the diffraction pattern does not comprise peaks at one or more, or both or each of, about 8.3, 10.5, and about 11.7 degrees, such as 8.3, 10.5, or 11.7±0.25, or ±0.2, or ±0.1 such as about ±0.05 degrees.

Most preferably, the Form I polymorph comprises all the characteristic peaks as shown by Example 1 hereinafter and the Form I polymorph may preferably be characterised by the X-ray powder diffractogram that is essentially that shown in FIG. 3 at ambient temperature.

The Form I polymorph may have a solubility in water, such as distilled or deionised water, at 23° C. of equal to or greater than about 9.0 mg/ml, such as from about 9.0 to about 12 mg/ml, for example, from about 9.3 to about 11 mg/ml, or from about 9.5 to about 10.5 mg/ml, such as about 9.6 mg/ml.

The Form I polymorph preferably comprises greater than about 92 wt. % crystalline ferric maltol based on the weight of the polymorph, such as greater than about 95 wt. %, preferably greater than about 96 wt. %, or about 98 wt. %, or about 99 wt. % such as about 99.8 wt. %.

The melting point of the Form I polymorph is typically about 300° C., such as 299.8° C.±0.5° C.

Alternatively, or in addition, the Form I polymorph, as defined in any of the above embodiments, may be characterised by a melting point of about 300° C., such as 299.8° C.±0.5° C.

Form II:

The form II polymorph preferably comprises a characteristic crystalline peak with 2-Theta value (in degrees) of around (i.e. at about or at approximately) 8.3±0.25, or ±0.2, or ±0.1 such as about ±0.05 degrees. The diffraction pattern typically does not comprise peaks at one or more, or all, or each of, about 6.9, 7.4, 9.3, 9.5, 10.5, 11.4 or about 13.7 degrees, such as 11.4 or 13.8±0.25, or ±0.2, or ±0.1 such as about ±0.05 degrees.

Preferably the Form II polymorph comprises characteristic crystalline peaks with 2-Theta values (in degrees) of around (i.e. at about or at approximately) 8.3 and 11.8 degrees±0.25, or ±0.2, or ±0.1 such as about ±0.05 degrees and, optionally, wherein the diffraction pattern does not comprise peaks at two or more of about 11.4, 12.8, 16.9, or 19.6±0.2, or ±0.1 such as about ±0.05 degrees.

The Form II polymorph alternatively comprises characteristic crystalline peaks with 2-Theta values (in degrees) of around (i.e. at about or at approximately) 8.3 and 11.8 degrees±0.2, or ±0.1 such as about ±0.05 degrees and wherein the diffraction pattern does not comprise peaks at 11.4 and/or 19.6±0.2, or ±0.1 such as about ±0.05 degrees.

Preferably the Form II polymorph comprises characteristic crystalline peaks with 2-Theta values (in degrees) of around (i.e. at about or at approximately) each of 8.3, 11.8, 13.4, 14.5, and 15.6, and, optionally, one or more, two or more, three or more, or each of, 15.5, 16.7, 21.1, 22.8, and 24.6 degrees±0.25, or ±0.2, or ±0.1 such as about ±0.05 degrees Typically, the Form II polymorph is characterised by a powder X-ray diffraction pattern comprising one or more further peaks expressed in degrees 2-theta selected from about 11.8, 12.5, 13.4, 14.5, 15.5, 15.6, 16.2, 16.7, 18.7, 19.2, 19.9, 20.6, 21.1, 22.8, 23.7, 24.6, 25.1, 25.7, 27.1, or 29.1±0.2, or ±0.1 such as about ±0.05 degrees.

More preferably, the Form II polymorph is characterised by a powder X-ray diffraction pattern comprising two or more, three or more, four or more or five or more further peaks expressed in degrees 2-theta selected from about 11.8, 12.5, 13.4, 14.5, 15.5, 15.6, 16.2, 16.7, 18.7, 19.2, 19.9, 20.6, 21.1, 21.7, 22.8, 23.7, 24.6, 25.1, or 25.7±0.2, or ±0.1 such as about ±0.05 degrees.

For example, the Form II polymorph may be characterised by a powder X-ray diffraction pattern comprising peaks expressed in degrees 2-theta at each of about 8.3, 11.8, 12.5, 13.4, 14.5, 15.5, 15.6, 16.2, 16.7, 18.7, 19.2, 19.9, 20.6, 21.1, 22.8, 23.7, 24.6, 25.1, and 25.7, and, optionally, 27.1 and 29.1±0.2, or ±0.1 such as about ±0.05 degrees, and, optionally, wherein the diffraction pattern does not comprise peaks at one or more or all of about 11.4, 12.7, 16.9, or 19.6±0.2, or ±0.1 such as about ±0.05 degrees, preferably 11.4±0.2, or ±0.1 such as about ±0.05 degrees.

Most preferably, the Form II polymorph comprises all the characteristic peaks as shown by Example 2 hereinafter and the Form II polymorph may be characterised by the X-ray powder diffractogram that is essentially that shown in FIG. 5 at ambient temperature.

The Form II polymorph may have a solubility in water, such as distilled or deionised water, at 23° C. of less than or equal to 7.0 mg/ml, such as from about 4.5 to about 6.9 mg/ml, for example, from about 5 to about 6.5 mg/ml, or from about 5.5 to about 6.2 mg/ml, such as about 5.9 mg/ml.

The Form II polymorph preferably comprises greater than 70%, 80%, or 90%, such as greater than 95%, or greater than 99% by weight crystalline ferric maltol based on the weight of the polymorph.

The melting point of the Form II polymorph is typically about 294° C., such as about 293.7° C.±1° C.

Alternatively, or in addition, the Form II polymorph, as defined in any of the above embodiments, may be characterised by a melting point of about 294° C., such as about 293.7° C.±1° C.

Form III:

The Form III polymorph preferably comprises a characteristic crystalline peak with 2-Theta value (in degrees) of around (i.e. at about or at approximately) 7.4±0.3, ±0.25, or 0.2, or ±0.1 such as about ±0.05 degrees. The diffraction pattern typically does not comprise peaks at one or more, or two or more, or three or more or each of, about 6.9, 8.3, 9.5, 11.3, 12.0, 12.5, 12.9, 14.5, or about 15.8 degrees, such as 6.9, 9.5, 11.3±0.25, or ±0.2, or ±0.1 such as about ±0.05 degrees.

The Form III polymorph is typically a solvate which comprises, for example, 1-4-dioxane, in the crystal structure.

Preferably the Form III polymorph comprises characteristic crystalline peaks with 2-Theta values (in degrees) of around (i.e. at about or at approximately) 7.4 and 9.3 and, optionally, 22.5 degrees±0.2, or ±0.1 such as about ±0.05 degrees and, optionally, wherein the diffraction pattern does not comprise peaks at two or more of about 9.5, 11.4, 12.9, 16.3, 19.6, 19.8, and 22.9±0.1 such as about ±0.05 degrees.

The Form III polymorph alternatively comprises characteristic crystalline peaks with 2-Theta values (in degrees) of around (i.e. at about or at approximately) each of 7.4 and 9.3 and 22.5 degrees±0.2, or ±0.1 such as about ±0.05 degrees.

Preferably the Form III polymorph comprises characteristic crystalline peaks with 2-Theta values (in degrees) of around (i.e. at about or at approximately) each of 7.4, 9.3, 22.1, 22.5 and 23.6 and, optionally, one or more, two or more, three or more, or each of, 11.6, 13.6, 14.0, 15.1, 17.0, 18.2, 24.9 and 27.4 degrees±0.2, or ±0.1 such as about ±0.05 degrees Typically, the Form III polymorph is characterised by a powder X-ray diffraction pattern comprising one or more further peaks expressed in degrees 2-theta selected from about 9.3, 10.5, 11.6, 13.6, 14.0, 15.1, 17.0, 17.7, 18.2, 18.7, 20.5, 21.2, 22.1, 22.5, 23.6, 24.9, 27.4 or 30.6±0.2, or ±0.1 such as about ±0.05 degrees.

More preferably, the Form III polymorph is characterised by a powder X-ray diffraction pattern comprising two or more, three or more, four or more or five or more further peaks expressed in degrees 2-theta selected from about 9.3, 10.5, 11.6, 13.6, 14.0, 15.1, 17.0, 17.7, 18.2, 18.7, 20.5, 21.2, 22.1, 22.5, 23.6, 24.9, 27.4 or 30.6±0.2, or ±0.1 such as about ±0.05 degrees.

For example, the Form III polymorph may be characterised by a powder X-ray diffraction pattern comprising peaks expressed in degrees 2-theta at each of about 7.4, 9.3, 11.6, 13.6, 14.0, 15.1, 17.0, 17.7, 18.2, 18.7, 20.5, 21.2, 22.1, 22.5, 23.6, 24.9, and 27.4±0.2, or ±0.1 such as about ±0.05 degrees.

Most preferably, the Form III polymorph comprises all the characteristic peaks as shown by Example 3 hereinafter and the Form III polymorph may be characterised by the X-ray powder diffractogram that is essentially that shown in FIG. 7 at ambient temperature.

The Form III polymorph preferably comprises greater than 70%, 80%, or 90%, such as greater than 95%, or greater than 99% by weight crystalline ferric maltol based on the weight of the polymorph.

The melting point of the Form III polymorph is typically about 301° C., such as 301° C.±0.5° C.

Alternatively, or in addition, the Form III polymorph, as defined in any of the above embodiments, may be characterised by a melting point of about 301° C., such as 301° C.±0.5° C.

Form IV:

The form IV polymorph preferably comprises a characteristic crystalline peaks with 2-Theta values (in degrees) of around (i.e. at about or at approximately) 9.5 and 14.5±0.2, or ±0.1 such as about ±0.05 degrees. The diffraction pattern typically does not comprise peaks at one or more, or two or more, or three or more or each of, about 6.9, 8.3, 10.5, 11.7, 12.0, 12.2, 12.5, 13.0, 13.4, and about 15.8 degrees, such as 6.9, 8.3, 11.7±0.25, or ±0.2, or ±0.1 such as about ±0.05 degrees.

Form IV is typically not a solvate and does not generally comprise solvent in the crystal structure.

Preferably the Form IV polymorph comprises characteristic crystalline peaks with 2-Theta values (in degrees) of around (i.e. at about or at approximately) 9.5 and 14.5 and, optionally, 15.5 degrees±0.2, or ±0.1 such as about ±0.05 degrees.

The Form IV polymorph alternatively comprises characteristic crystalline peaks with 2-Theta values (in degrees) of around (i.e. at about or at approximately) 9.5, 14.5 and 15.5 degrees±0.2, or ±0.1 such as about ±0.05 degrees.

Preferably the Form IV polymorph comprises characteristic crystalline peaks with 2-Theta values (in degrees) of around (i.e. at about or at approximately) each of 9.5, 11.4, 12.8, 14.5 and 15.5, and, optionally, one or more, two or more, three or more, or each of, 19.9, 23.1, 25.0 and 25.8 degrees±0.2, or ±0.1 such as about ±0.05 degrees Typically, the Form IV polymorph is characterised by a powder X-ray diffraction pattern comprising one or more further peaks expressed in degrees 2-theta selected from about 11.4, 12.8, 13.7, 15.5, 18.5, 19.9, 23.1, 25.0 and 25.8±0.2, or ±0.1 such as about ±0.05 degrees.

More preferably, the Form IV polymorph is characterised by a powder X-ray diffraction pattern comprising two or more, three or more, four or more or five or more further peaks expressed in degrees 2-theta selected from about 11.4, 12.8, 13.7, 15.5, 18.5, 19.9, 23.1, 25.0 and 25.8±0.2, or ±0.1 such as about ±0.05 degrees.

For example, the Form IV polymorph may be characterised by a powder X-ray diffraction pattern, comprising peaks expressed in degrees 2-theta at each of 9.5, 11.4, 12.8, 14.5, 15.5, 19.9, and 23.1±0.2, or ±0.1 such as about ±0.05 degrees.

Most preferably, the Form IV polymorph comprises all the characteristic peaks as shown by Example 4 hereinafter and the Form IV polymorph may be characterised by the X-ray powder diffractogram that is essentially that shown in FIG. 9 at ambient temperature.

The Form IV polymorph preferably comprises greater than 70%, 80%, or 90%, such as greater than 95%, or greater than 99% by weight crystalline ferric maltol based on the weight of the polymorph.

The melting point of the Form IV polymorph is typically about 303° C. such as 302.8° C.±1 or ±0.5° C.

Alternatively, or in addition, the Form IV polymorph, as defined in any of the above embodiments, may be characterised by a melting point of about 303° C. such as 302.8° C.±1 or ±0.5° C.

The polymorphs of the invention are preferably substantially crystallographically pure. By "substantially crystallographically pure" we mean a crystalline form of the compound, as judged by X-ray Powder Diffraction (XRPD) measurements, that contains less than about 5%, more preferably less than about 3% and especially less than about 1% of other crystalline forms of the compound and/or amorphous forms of the compound.

Thus, preferably polymorph Form I is substantially free of Forms II to IV, as determined by, for example, XRPD, solid state $^1$H NMR, Raman or Near IR. Also, preferably polymorph Form II is substantially free of Forms I, III and IV, as determined by, for example, XRPD, solid state $^1$H NMR, Raman or Near IR. Also, Form III is preferably substantially free of Forms I, II and IV and Form IV is preferably substantially free of Forms I, II and III as determined by, for example, XRPD, solid state $^1$H NMR, Raman or Near IR. In this aspect of the invention, "substantially free of" means that the sum of the amounts of other forms is less than 50% by weight, more preferably equal to or less than 20%, more preferably equal to or less than 10% by weight, more preferably equal to or less than 5% by weight, more preferably equal to or less than 1% by weight, or preferably equal to or less than 0.1%, such as about 0% based on the amount of the polymorph.

It has been found that, surprisingly, the process conditions, such as batch size, solvent for recrystallization or slurrying, type of seed crystal, slurry conditions and washing or drying conditions, can affect which polymorph of ferric maltol is produced.

The invention provides a process for the preparation of a ferric maltol polymorph, such as Form I or Form II which comprises combining ferric citrate with maltol anions to form ferric maltol polymorph and wherein the process comprises the use of a ferric maltol seed crystal, such as a seed crystal of Form I and/or Form II polymorph as described herein.

The Form III polymorph, as defined herein, may be produced by a process comprising combining the Form I and/or Form II polymorph, as defined herein, with a solution comprising 1,4-dioxane to form a mixture. The solution may also comprise water. The temperature of the solution or mixture may be greater than about 30° C., such as from 31 to 50° C. such as from 35 to 45° C., for example about 40° C.

The mixture may be stirred for a period of from 30 minutes to 2 hours, such as about 1 hour.

Preferably, after stirring for a period of time, the mixture is filtered, such as polish filtered. A person skilled in the art will understand that polish filtering, such as by using a sinter glass filter, can remove substantially all solid particles from a solution.

Preferably the process to produce polymorph Form III does not comprise the use of a seed crystal.

The mixture, which has preferably been polish filtered, is preferably cooled to ambient temperature and, optionally, filtered under suction to obtain a solid. The solid obtained can be dried, for example, in a vacuum oven, at a temperature of, for example, at least 40° C., such as about 45° C. The solid obtained comprises polymorph Form III.

The Form IV polymorph, as defined herein, may be produced by a process comprising combining Form I and/or Form II polymorph, as defined herein, with a solution comprising one or more of 2-chlorobutane, TBME (tert-butyl methyl ether), or 3-methyl-1-butanol to form a mixture, followed by crystallisation.

The Form IV polymorph may be obtained following cooling crystallisation from the above solvents, such as mixed solvent cooling crystallisation.

Preferably the process to produce polymorph Form IV does not comprise the use of a seed crystal.

The process of the invention for forming Form I or Form II polymorph, in any of the embodiments described herein, may comprise the following steps:
 (a) forming an aqueous solution comprising ferric citrate, such as a solution of ferric citrate in an aqueous solution, such as water;
 (b) combining maltol with a base in an aqueous solution, such as water, to form a solution comprising maltol anions;
 (c) combining the aqueous solution of ferric citrate with the aqueous solution comprising maltol anions, wherein a seed crystal of ferric maltol (polymorph Form I and/or Form II) is added; and
 (d) isolating the polymorph of ferric maltol.

Typically step (a) comprises heating the ferric citrate in the solution followed by cooling, for example to a temperature of less than or equal to about 35° C., such as from about 20 to 30° C.

In step (b), the temperature of the solution is preferably maintained at a temperature of about 15 to 30° C., such as from about 20 to 25° C. The base may be any suitable base but is preferably an alkali metal hydroxide, such as sodium or potassium hydroxide.

For step (c), preferably a molar excess of the maltol anions to iron over the 3:1 molar amount required to form ferric maltol is preferably used. For example, the molar ratio of the maltol anions to ferric iron is preferably greater than 3:1, for example the molar ratio of maltol anions to iron may be about 3.5:1 to 3.05:1, such as about 3.15:1.

The temperature in step (c) may be maintained at less than about 35° C., such as from about 20 to about 25° C. The ferric maltol seed crystal is preferably added in an amount of less than about 1.5% w/w based on the theoretical yield of ferric maltol obtainable with the amounts of ferric citrate and maltol used, such as preferably about 0.1 to 1.0% w/w or up to 0.5% w/w of the theoretical or maximum possible yield of ferric maltol.

Optionally the combined solutions are stirred. The stirring may be continued for a period of at least 10 minutes, such as 1 hour or greater, such as from 2 to 6 hours.

A slurry of ferric maltol in an aqueous solution, such as water, generally comprising soluble by-products, may be formed during step (c) and the slurry may be left, such as with stirring, at ambient temperature for a period of time, such as at least 10 minutes. The slurry may alternatively be left for longer than 10 minutes, such as at ambient temperature and with optional stirring, for example for at least 30 minutes or at least 2 hours.

The slurry typically comprises a precipitate of the ferric maltol in the solution i.e., a suspension of ferric maltol. The slurry is preferably washed with water, for example, at least three times, to remove soluble by-products, and the resulting ferric maltol dried. The drying may be carried out using any means known in the art. A filter bed dryer may be used.

The process of forming polymorph Form I typically comprises seeding, such as with a seed crystal comprising polymorph Form I and/or Form II, isolating, such as by filtration, washing the precipitate comprising formed polymorph Form I, such as with water, and drying the washed polymorph for a period of, for example, from 1 to 12 hours, such as in a vacuum oven at a temperature greater than 30° C., such as greater than 45° C., or at a temperature of greater than 60° C. without vacuum. The slurry comprising the precipitate is preferably stirred for less than 30 hours, such as from 2 to 24 hours at ambient temperature, such as from about 5 to about 40° C., preferably about 10 to about 30° C.

The process of forming polymorph Form II typically comprises seeding, such as with a seed crystal comprising polymorph Form I and/or Form II, isolating, such as by filtration, washing the precipitate comprising formed polymorph Form II, such as with water, and drying the washed polymorph for a period of, for example, greater than 12 hours, such as in a vacuum oven at a temperature greater than 30° C., such as greater than 45° C., or at a temperature of greater than 60° C. without vacuum. The slurry comprising the precipitate is preferably stirred for greater than 30 hours, such as from 36 to 48 hours at a temperature of at least 35° C., such as about 40° C.

The Form II polymorph may also be formed by stirring an aqueous slurry comprising Form I for an extended period of time, such as at least 48 hours at a temperature of greater than or at least 35° C., such as about 40° C. or higher.

The seed crystal used to produce the Form I polymorph is preferably a seed crystal comprising Form I. The crystal may be obtained as described in Example 1.

The seed crystal used to produce the Form II polymorph may be seed crystals comprising the Form I and Form II polymorphs, which may be prepared as described herein.

The process may be carried out as a continuous or batch process. Where the process is carried out as a batch process the amount of the batch can, surprisingly, affect which polymorph form is produced.

When the batch size is less than or equal to 20 kg, such as from 1 to 18 kg or from 5 or 10 to 16 kg, the Form I polymorph may be produced. This may be due to a reduced drying time. Alternatively, when the batch size is greater than 20 kg, such as from 21 to 100 kg, or from 25 to 50 kg, such as 22 to 28 kg, the Form II polymorph may be produced due to an extended drying time. If the batch size is greater than 20 kg and the seed crystal is a mixture of Form I and Form II polymorphs, then Form II polymorph can be produced. If the batch size is greater than 20 kg and the seed crystal is of Form I polymorph, then a mixture of Form I and Form II can be produced.

As may be appreciated by the skilled person, the crystalline form that is obtained depends upon both the kinetics and the thermodynamics of the crystallisation process. Under certain thermodynamic conditions (solvent system, temperature, pressure and concentration of the compound of the invention), one crystalline form may be more stable than another (or indeed any other). However, other crystalline forms that may have, in comparison, a relatively low thermodynamic stability, may be kinetically-favoured. Thus, in addition, kinetic factors, such as time, impurity profile, agitation, the presence of seeds, etc. may also influence which forms appear. Thus, the procedures discussed herein may be adapted by the skilled person as appropriate in order to obtain the particular crystalline form of ferric maltol.

As stated hereinbefore, the polymorphs of the invention may also be characterised by a powder X-ray diffraction pattern that is essentially according to that shown in FIG. 3, FIG. 5, FIG. 7 or FIG. 9 attached hereto at ambient temperature (see Examples 1 to 4). The skilled person will appreciate that a polymorph form shows "essentially" the same powder X-ray diffraction pattern as another when it was clear to that skilled person from the respective patterns (i.e. the relative spacing of the peaks, allowing for experimental error, such as preferred orientation of the sample and respective instrument settings (e.g. apparatus type, standardization and/or calibration)) that the same crystalline form has been formed as for each of Form I, Form II, Form III and Form IV.

The polymorphs of the invention can have a surprisingly improved physical and/or chemical stability.

The term "stable" as defined herein includes chemical stability and solid state stability.

By "chemical stability", we include that the compound can be stored in an isolated solid form, or in the form of a solid formulation in which it may be provided in admixture with pharmaceutically acceptable carriers, diluents or adjuvants, under normal storage conditions, with an insignificant degree of chemical degradation or decomposition.

By "solid state stability", we include that the compound can be stored in an isolated solid form, or in the form of a solid formulation in which it may be provided in admixture with pharmaceutically acceptable carriers, diluents or adjuvants, under normal storage conditions, with an insignificant degree of solid state transformation (e.g. crystallisation, recrystallisation, loss of crystallinity, solid state phase transition, hydration, dehydration, solvatisation or desolvatisation).

Examples of "normal storage conditions" include temperatures of between minus 80 and plus 50° C. (preferably between 0 and 40° C. and more preferably ambient temperature, such as between 15 and 30° C.), pressures of between 0.1 and 2 bars (preferably atmospheric pressure), and/or exposure to 460 lux of UV/visible light, for prolonged periods (i.e. greater than or equal to six months). Under such, conditions, the polymorphs of the invention may be found to be less than about 15%, more preferably less than about 10%, and especially less than about 5%, chemically degraded/decomposed, or solid-state transformed, as appropriate. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

The term "normal storage conditions" may also include relative humidities of between 5 and 95% (preferably 10 to 60%). However, in the case of certain crystalline forms according to the invention, changes in conformation or crystal structure by hydration and/or dehydration may occur as a result of prolonged exposure to certain extremes of relative humidities, at normal temperatures/pressures.

The preparation and characterisation of compounds of the invention are described hereinafter. Different crystalline forms of the compounds of the invention may be readily characterised using X-ray powder diffraction (XRPD) methods, for example as described hereinafter.

The polymorphs of the invention may be isolated using techniques that are well known to those skilled in the art, for example decanting, filtering and/or centrifuging.

We have found that, by employing the crystallisation processes described herein, it is possible to produce compounds of the invention with a high chemical purity.

When the polymorphs of the invention are prepared as described herein, the resultant polymorph may be in a form which has improved chemical and solid state stability, as mentioned hereinbefore, as well as improved solubility and hygroscopicity profiles compared to other polymorphs of ferric maltol.

The polymorphs of the invention are useful because they possess pharmacological activity. They are therefore indicated as pharmaceuticals.

Polymorphs of the invention are indicated both in the therapeutic and/or prophylactic treatment of iron deficiency with or without anaemia, such as iron deficiency anaemia.

The term "subject" as used herein includes mammalian animals, for example, humans, as well as animals, such as cows, dogs, cats, horses, rabbits, and pigs. Hence, the uses and method of treatment discussed above may include the treatment of a human or animal body.

The term "effective amount" refers to an amount of a polymorph, which confers a therapeutic effect on the treated patient. The effect may be objective (e.g. measurable by some test or marker) or subjective (e.g. the subject gives an indication of or feels an effect).

The polymorphs and compositions of the invention may be administered orally, intravenously, subcutaneously, buccally, rectally, dermally, nasally, tracheally, bronchially, sublingually, by any other parenteral route or via inhalation, in a pharmaceutically acceptable dosage form. For instance, the pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the polymorphs and compositions of the invention are administered orally.

The polymorphs of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a polymorph of the invention, as hereinbefore defined, in admixture with a pharmaceutically acceptable adjuvant, diluent and/or carrier. Such formulations may be administered as described hereinbefore. The polymorph of the invention (i.e. the crystalline form) that is the active ingredient of the pharmaceutical formulation may be milled or ground into smaller particles.

Depending on e.g. potency and physical characteristics of the polymorph of the invention (i.e. active ingredient), pharmaceutical formulations that may be mentioned include those in which the active ingredient (i.e. the polymorph of the invention) is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of polymorph of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a polymorph of the invention, as hereinbefore defined, with a pharmaceutically-acceptable adjuvant, diluent or carrier.

Polymorphs of the invention may also be combined with other therapeutic agents, for instance those that are also useful in the treatment of iron deficiency with or without anaemia, such as iron deficiency anaemia. Alternatively, the polymorphs of the invention may be the sole therapy used. Polymorphs and compositions of the invention may also be combined with other therapies.

Depending on the disorder, and the patient to be treated, as well as the route of administration, the polymorphs and compositions of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a polymorph of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Wherever the word "about" is employed herein, for example in the context of amounts (e.g. values, weights, volumes, moles), temperatures, degrees of crystallinity, degrees of degradation, degrees of purity, degrees of dissolution and doses of active ingredients, it will be appreciated that such variables are approximate and as such may vary by ±10%, for example ±5% and preferably ±2% (e.g. ±1%) from the numbers specified herein.

The polymorphs of the invention have the advantage that they can be in a form which provides for improved ease of handling, and may be produced in forms which have improved chemical and solid state stability when compared to other polymorph forms of ferric maltol. Thus, the polymorphs of the invention may be stable when stored over prolonged periods. In particular, the polymorph Form II may have improved thermodynamic stability, compared to other polymorph forms of ferric maltol.

The polymorphs of the invention may also have improved solubility and hygroscopicity profiles when compared to other polymorph forms of ferric maltol.

Compounds of the invention i.e., polymorph Forms I, II, III and IV may also have the advantage that they may be prepared in good yields, in a higher purity, in less time, more conveniently, and at a lower cost, than other polymorph forms of ferric maltol.

Compounds of the invention i.e., polymorph Forms I, II, III and IV may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over other polymorphs of ferric maltol, whether for use in the above-stated indications or otherwise.

In a further aspect, the present invention relates to a pharmaceutical composition according to the invention together with a pharmaceutically acceptable diluent or carrier.

By "pharmaceutically acceptable" we include the normal meaning that the carriers must be "acceptable" in the sense of being compatible with the active ingredient (the ferric maltol) and not deleterious to the recipients thereof.

The composition may be in the form of a solid, such as a powder, capsule or tablet, or liquid. Suitable solid diluents and carriers include starch, dextrin and magnesium stearate. Stabilising and suspending agents such as methylcellulose and povidone and other tableting agents such as lactose and flow aids such as Aerosil 2000™ may also be used.

Particularly useful diluents and carriers are wetting agents or surfactants, preferably non-ionic or ionic surfactants. Examples of suitable non-ionic surfactants include polyoxyl-10-oleyl ether and polysorbates. An example of a suitable ionic surfactant is sodium lauryl sulfate.

Liquid carriers may be sterile and pyrogen free: examples are saline and water.

The polymorphs and compositions of the present invention can provide particular advantages in relation to the formulation of iron complexes. Liquid formulations of the iron compounds may be particularly suitable for oral and parenteral administration. In such applications, the solubility of some known iron complexes is unsatisfactory.

The ferric maltol polymorphs and compositions comprising said forms may be formulated with a physiologically acceptable diluent or carrier for use as pharmaceuticals for veterinary or human use in a variety of ways. However, compositions in which the diluent or carrier is other than a non-sterile solution in water and/or an organic solvent are generally preferred. Thus, the ferric maltol may be applied as an aqueous, oily or emulsified composition incorporating a liquid diluent, which will, however, most usually be employed for parenteral administration and therefore may conveniently be sterile and pyrogen free. One form of composition of particular interest thus has the form of a sterile, injectable solution. Oral administration is, however, more generally to be preferred for the treatment of iron deficiency with or without anaemia in humans, and the compositions of the present invention are preferably given by that route.

For oral administration in humans it is more usual to use compositions incorporating a solid carrier, for example, starch, lactose, dextrin or magnesium stearate. Such solid compositions may conveniently be shaped, for example in the form of tablets, capsules (including spansules), etc. However, liquid preparations are especially useful for oral administration to patients who have difficulty in swallowing solid forms. Such difficulties are common in patients suffering from anaemias associated with arthritis.

Other forms of administration than by injection or through the oral route may also be considered, for example the use of suppositories.

More than one ferric maltol polymorph of the present invention may be contained in a pharmaceutical composition, although it is preferred that only a single polymorph is present, and other active compounds may also be included. Typical additives include compounds having the ability to facilitate the treatment of anaemia, such as folic acid. A zinc source may also be included.

Preferably the polymorphs and the compositions of the invention are suitable for use in medicine.

The polymorphs and compositions of the present invention are particularly useful for the treatment of serious anaemias arising from bleeding disorders, particularly of the gastrointestinal tract. Many of the patients with such disorders are intolerant of standard ferrous anti-anaemia compounds. Ferrous preparations can be contra-indicated or be the subject of warnings in such conditions. Furthermore, patients who may need blood transfusions or in-patient treatment with intravenous injections can be treated on an outpatient basis with the polymorphs and compositions of the present invention saving substantial costs of treatment.

The polymorphs and pharmaceutical compositions of the invention may be used in a method for the treatment of a subject to effect an increase in the levels of iron in the subject's body or bloodstream and/or the prevention and/or treatment of anaemia, such as iron deficiency with or without anaemia, which comprises administering to said subject an effective amount of composition as defined previously.

The polymorphs and compositions described herein are useful in the treatment of iron deficiency with or without anaemia. The term "iron deficiency" as used herein refers to iron deficiency without anaemia—this could be, for example, iron deficiency which has not progressed to anaemia. For the avoidance of doubt, iron deficiency with or without anaemia relates to all diseases and conditions associated with iron deficiency and for which treatment with iron would be therapeutically beneficial. Such diseases are those which are recognised as having iron deficiency as a complication or leading to signs and symptoms. Iron deficiency is also referred to as sideropenia or hypoferremia and results from a prolonged period of inadequate iron intake; deficiency in absorption and/or excessive blood (iron) loss.

Symptoms and signs of iron deficiency can be apparent before iron deficiency anaemia occurs and include but are not limited to fatigue, hair loss, twitches, irritability, dizziness, brittle or grooved nails, appetite disorders such as pica and pagophagia, impaired immune function, chronic heart failure, growth retardation, behaviour and learning problems in children, cognition in the elderly and Plummer-Vinson syndrome (PVS).

Conditions associated with iron deficiency anaemia include, but are not limited to chronic kidney disease (CKD), Systemic Lupus (SLE), rheumatoid arthritis, haematological cancers (e.g. Hodgkin's disease), chronic bacterial infection (e.g. osteomyelitis), viral hepatitis, HIV, AIDS, diseases of the gastrointestinal tract for example inflammatory bowel diseases (IBD) such as Crohn's disease and ulcerative colitis, gynaecological and obstetric situations such as heavy uterine bleeding, pregnancy and childbirth.

For example, the polymorphs of the invention may be used for improving cognition in the elderly. The term "elderly" may include, for example, mammals such as humans aged over 60, such as from 70 to 100 years old.

The polymorphs and compositions of the present invention may also be used in the treatments described in WO 2009/138761, which is incorporated by reference herein.

The invention is illustrated, but in no way limited, by the following examples, with reference to the enclosed figures in which:

FIG. 2 shows the DSC and TGA analysis for Form I polymorph.

FIG. 3 shows an X-ray powder diffractogram for the Form I polymorph, obtained by way of Example 1 (cps (intensity) values are plotted against ° 2-Theta values).

FIG. 4 shows the DSC and TGA analysis for Form II polymorph.

FIG. 5 shows an X-ray powder diffractogram for the Form II polymorph, obtained by way of Example 2 (cps (intensity) values are plotted against ° 2-Theta values).

FIG. 6 shows the DSC and TGA analysis for Form III polymorph.

FIG. 7 shows an X-ray powder diffractogram for the Form III polymorph, obtained by way of Example 3 (cps (intensity) values are plotted against ° 2-Theta values).

FIG. 8 shows the DSC and TGA analysis for Form IV polymorph.

FIG. 9 shows an X-ray powder diffractogram for the Form IV polymorph, obtained by way of Example 4 (cps (intensity) values are plotted against ° 2-Theta values).

Figure 1:
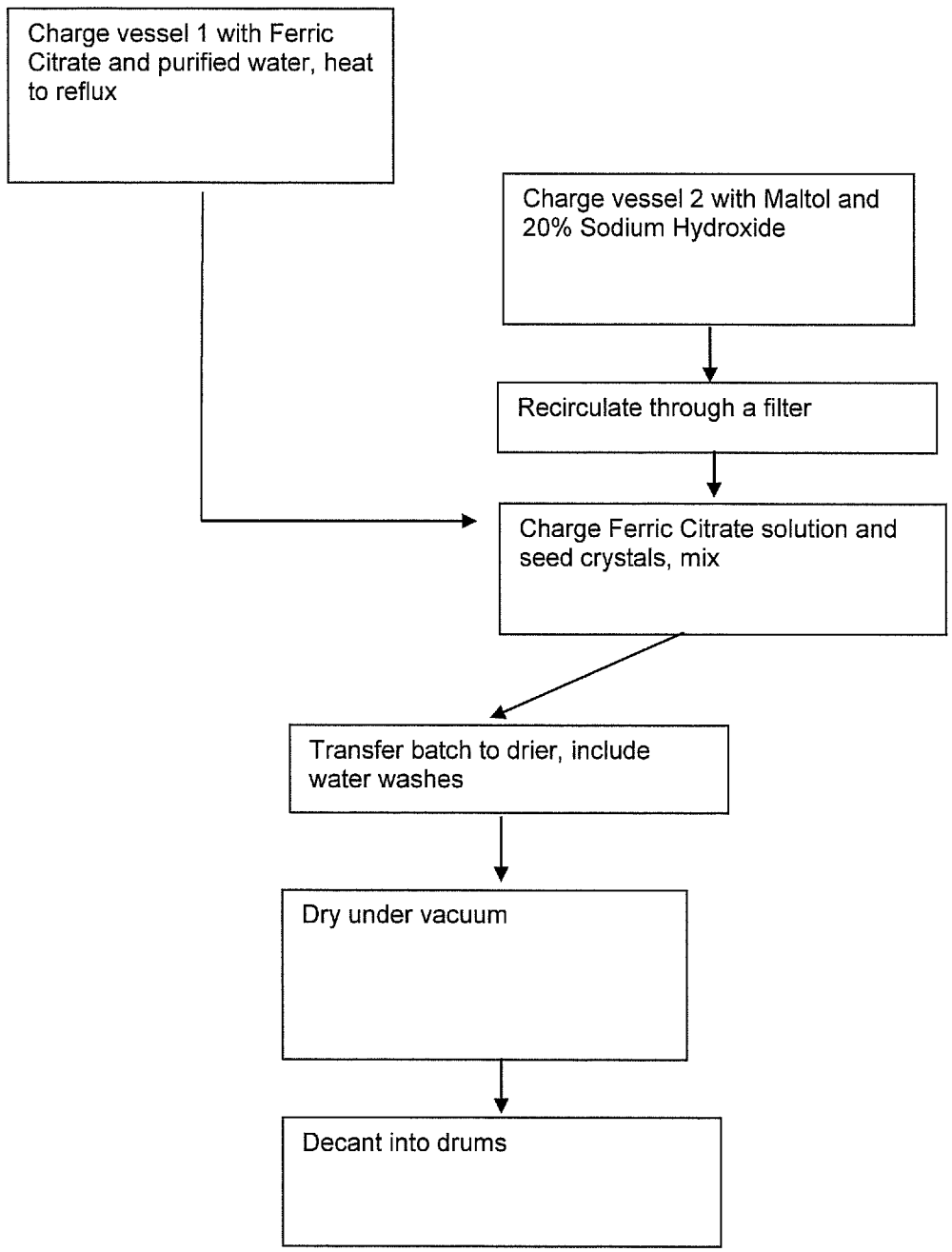
FIG. 1 shows the general process that can be used to prepare the different ferric maltol polymorphs with the modifications disclosed herein.

Preferences and options for a given aspect, embodiment, feature or parameter of the invention should, unless the context indicates otherwise, be regarded as having been disclosed in combination with any and all preferences and options for all other aspects, embodiments, features and parameters of the invention. For example, the preferred features of the polymorphs may be applied when the polymorph is used in the composition of the invention and the preferred features of the polymorph may be applied when the polymorph is used in the prevention or treatment of anaemia.

The listing or discussion of an apparently prior-published document in this specification should not necessarily be taken as an acknowledgement that the document is part of the state of the art or is common general knowledge.

The following non-limiting examples illustrate the invention and do not limit its scope in any way. In the examples and throughout this specification, all percentages, parts and ratios are by weight unless indicated otherwise. Average molecular weights are based on weight unless otherwise specified. It will be appreciated that the various percentage amounts of the different components that are present in the products of the invention, including any optional components, will add up to 100%.

General Procedures:

Details of how XRPD Data Obtained

The instrument conditions used to obtain the XRPD data were:

Instrument: PANalytical X'Pert PRO
Range: 3° 2θ to 35° 2θ in conventional reflection mode
Scan speed: 0.202004° s-1
Detector: PIXcel detector
Slit: ½°
Source: Copper K-alpha radiation
Voltage: 45 kV
Intensity: 40 mA X-Ray Powder Diffraction patterns were collected on a PANalytical X'Pert PRO diffractometer using Cu Kα radiation (45 kV, 40 mA), θ-θ goniometer, focusing mirror, divergence slit (½°), soller slits at both incident and diffracted beam (0.04 RAD), fixed mask (4 mm) and a PIXcel detector. The software used for data collection was X'Pert Data Collector, version 2.2j and the data was presented using X'Pert Data Viewer, version 1.2d.

XRPD patterns were acquired under ambient conditions via a transmission foil sample stage (polyimide—Kapton, 12.7 μm thickness film) using a PIXcel detector. The data collection range was 2.994-35° 2θ with a continuous scan speed of 0.202004° $s^{-1}$.

X-Ray Powder Diffraction Method Description

X-ray powder diffraction (XRPD) analysis can be performed on samples prepared according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York. X-ray diffraction analyses were performed using a Thermo ARL X'TRA (wavelength of X-rays 1.5418 Å, Cu source, Voltage 45 kV, filament emission 44 mA) for 152 minutes from 2 to 40°. Calculation of peak positions (° 2-theta) was done and they may vary in the range ±0.2° 2-theta.

It will be appreciated by a skilled person in the art that XRPD intensities may vary when measured for essentially the same crystalline form, for example, preferred orientation.

EXAMPLE 1: FORM I 9.04 kg ferric citrate was combined with 29 liters of purified water. Separately, 12.2 kg of maltol was combined with 15.2 liters of sodium hydroxide solution (20% w/w). The ferric citrate and sodium hydroxide were charged into a vessel with the addition of 4 liters of water and then stirred at 20 to 25° C. A seed was then added. The seed was 65 g of ferric maltol polymorph in 12 liters of water. The seed crystal was prepared by the same process as described in Example 1 but without the use of a seed crystal. The seed was added to the vessel to aid a consistent crystallisation/ precipitation. The mixture was held in the vessel, as a suspension, to allow crystal growth and then filtered and washed three times, each time with 13 liters of water. The resulting solid was dried at less than 80° C. and produced 13.25 kg of dried ferric maltol.

The ferric maltol in Example 1 was produced on a scale of 12 to 15 kg in different batches. The analysis of the ferric maltol produced showed the % w/w of iron present was about 12.8 to 13.0 and the % w/w of maltol present was about 87.6 to 89.3.

EXAMPLE 1a

Production of Ferric Maltol Via Recrystallisation with and without Seeding of Form II Ferric citrate (15 g, 6.12×10$^{-2}$ mol) was dissolved in water (60 ml) and heated under reflux with stirring to aid dissolution. The solution was then cooled to room temperature. In a separate reaction vessel, maltol (19.17 g, 0.152 mol) was placed in 6M sodium hydroxide (27 ml) with stirring at room temperature until the solid had fully dissolved. The solution was then polish filtered.

The ferric citrate solution was added to the sodium maltol solution with stirring at room temperature. The formation of a precipitate was observed after approximately 15 minutes. The mixture was sampled after 2 and 4 hours of stirring. XRPD analysis shows that the solids were comparable to Form I. The slurry was then left to stir overnight. The mixture was filtered under suction and the majority of the solid was dried in a vacuum oven (45° C.). A small portion of the solid (3 g) was taken and dried at 80° C. without vacuum. Both solids were shown to be Form I polymorph by XRPD after drying.

The reaction crystallisation for the generation of ferric maltol performed without seeding of Form II produces Form I, when the solid is dried at 45° C. under vacuum and at 80° C. without vacuum.

The reaction was repeated with seeding of Form II (150 mg) after the addition of the ferric citrate solution to the sodium maltol solution. XRPD analysis shows that the samples taken after 2 hours and 20 hours at ambient temperature are comparable to Form I. A mixture of forms was noted after the mix was left for an overnight stir at 25° C. Form II was isolated after a further overnight stir at 40° C. This information supports previous conclusions that Form II will eventually become the dominant form after an adequate amount of time for equilibration.

The XRPD pattern of the form obtained by way of Example 1a is shown in FIG. 3.

EXAMPLE 2: FORM II

The ferric maltol in Example 2 was produced using the general method as described in Example 1 but the ferric maltol was produced on larger scale batches of 24 to 33 kg.

The analysis of the ferric maltol produced showed the % w/w of iron present was about 12.7 and the % w/w of maltol present was about 88 to 88.6.

The XRPD pattern of the Form II polymorph obtained by way of Example 1a is shown in FIG. 5.

The analysis of the ferric maltol produced showed the % w/w of iron present was about 12.7 to 12.9 and the % w/w of maltol present was about 86.7 to 87.1 in different batches. The ferric maltol seed crystal used in Example 2 was, however, a seed crystal of Form I and II polymorph.

The precipitated ferric maltol was also held in the wet slurry longer than for Example 1.

The XRPD pattern of the Form II polymorph obtained by way of Example 1a is shown in FIG. 5.

EXAMPLE 3: FORM III

Previous experiments had indicated that slurries comprising 1,4-dioxane generated a new polymorph form, which has been characterised as Form III. Production of this new form was completed on a larger scale to perform further analysis on the sample.

Form III

A mixture of Form I and Form II polymorphs (100 mg) was placed in 15 volumes of 5% water/1,4-dioxane at 40° C. and stirred for one hour. The mixture was polish filtered before being cooled to ambient temperature and filtered under suction. The solid obtained was dried in a vacuum oven (45° C.) overnight.

XRPD analysis (7) shows that the solid obtained is consistent with polymorph Form III. DSC and TGA results suggest that the solid exists a solvated form. HPLC analysis indicated a chemical purity of 99.8%.

The XRPD for Form III is shown in FIG. 7.

EXAMPLE 4: FORM IV

Analysis of Form IV

Solids obtained from 2-chlorobutane and TBME in the mixed solvent cooling crystallisation of a mixture of Form I and Form II polymorphs were not directly comparable to Form I or Form II polymorphs. It was therefore concluded that a new form or a mixture of forms had been isolated.

This new form is comparable to that generated from 3-methyl-1-butanol and will be termed Form IV. The solids were analysed using DSC.HPLC analysis gave a chemical purity of 99.3% for the solid.

The XRPD for Form IV is shown in FIG. 9.

EXAMPLE 5

The solubility in pure water of samples of the different polymorphs was assessed at 23° C. The results are set out in the following table.

| Polymorph | Solubility (mg/ml) |
|---|---|
| Form I | 9.6 |
| Form II | 5.9 |

EXAMPLE 6

Competitive Slurries

Form IV (10 mg) was placed in water (1 ml) with 10 mg of Form I and Form II and stirred overnight at ambient temperature. A second slurry was set up to also include a further polymorph. Mixtures were filtered under suction and dried in a vacuum oven (45° C.).

XRPD data shows that the product from the slurry involving Forms I, and IV generated Form II. The slurry also involving another polymorph produced a mixture of forms.

The same experimental procedure was applied to a slurry involving Forms I, II, III and IV. The initial test was performed in water and a second was carried out in ethyl acetate. XRPD analysis shows that Form II was isolated. This work supports previous conclusions that Form II is the dominant form.

CONCLUSIONS

Form III typically exists as a solvated form with a chemical purity 99.8%.

Form IV typically is a non-solvated form.

Competitive slurries indicate that Form II is the dominant form.

The reaction crystallisation showed that Form I can be isolated under certain conditions when the reaction is performed without seeding of Form II. Form II can be generated with seeding when the mixture is stirred for an extended period of time at 40° C.

The invention claimed is:

1. Form II polymorph of ferric maltol characterized by a powder X-ray diffraction pattern comprising a characteristic crystalline peak expressed in degrees 2-theta at 8.3±0.25 degrees, and two or more further peaks expressed in degrees 2-theta selected from about 11.8, 12.5, 13.4, 14.5, 15.5, 15.6, 16.2, 16.7, 18.7, 19.2, 19.9, 20.6, 21.1, 22.8, 23.7, 24.6, 25.1, 25.7, 27.1, or 29.1±0.2, or ±0.1 such as about ±0.05 degrees.

2. The polymorph of claim 1, characterised by a powder X-ray diffraction pattern comprising three or more, or four or more further peaks expressed in degrees 2-theta selected from about 11.8, 12.5, 13.4, 14.5, 15.5, 15.6, 16.2, 16.7, 18.7, 19.2, 19.9, 20.6, 21.1, 22.8, 23.7, 24.6, 25.1, 25.7, 27.1, or 29.1±0.2, or ±0.1 such as about ±0.05 degrees.

3. The polymorph of claim 1, wherein the polymorph is characterised by a powder X-ray diffraction pattern comprising peaks expressed in degrees 2-theta at each of about 8.3, 11.8, 13.4, 14.5, and 15.6, and, optionally, one or more, two or more, three or more or each of 15.5, 16.7, 21.1, 22.8, and 24.6 degrees±0.25, or ±0.2, or ±0.1 such as about ±0.05 degrees.

4. A process for the preparation of a form as claimed in claim 1, which comprises combining ferric citrate with maltol anions in solution to form ferric maltol polymorph Form II, wherein the process comprises the use of a ferric maltol seed crystal comprising Form I and/or Form II polymorph.

5. Form I polymorph of ferric maltol characterized by a powder X-ray diffraction pattern comprising characteristic crystalline peaks expressed in degrees 2-theta at 15.6 and 22.5±0.25 degrees, and one or more further peaks expressed in degrees 2-theta selected from about 11.4, 12.8, 13.7, 16.9, 18.5, 19.6, 20.0, 20.7, 23.0, 23.8, 25.2 or 25.8±0.25 or ±0.2, or ±0.1 such as about ±0.05 degrees.

6. The polymorph of claim 5, wherein the diffraction pattern does not comprise peaks at any one of about 8.3 and about 11.7 degrees.

7. The polymorph of claim 5, characterised by a powder X-ray diffraction pattern comprising two or more, three or more, or four or more further peaks expressed in degrees 2-theta selected from about 11.4, 12.8, 13.7, 16.9, 18.5, 19.6, 20.0, 20.7, 23.0, 23.8, 25.2 or 25.8 degrees.

8. The polymorph of claim 5, wherein the polymorph comprises characteristic crystalline peaks with 2-Theta values (in degrees) at each of 11.4, 15.6, 16.9, 22.5, and 23.8.

9. A process for the preparation of a form as claimed in claim 5, which comprises combining ferric citrate with maltol anions to form a mixture comprising ferric maltol polymorph Form I and wherein the process comprises the use of a ferric maltol seed crystal comprising Form I.

10. Form III polymorph of ferric maltol characterized by a powder X-ray diffraction pattern comprising a peak expressed in degrees 2-theta at 7.4±0.25 degrees, and two or more, three or more, four or more or five or more further peaks expressed in degrees 2-theta selected from about 9.3, 10.5, 11.6, 13.6, 14.0, 15.1, 17.0, 17.7, 18.2, 18.7, 20.5, 21.2, 22.1, 22.5, 23.6, 24.9, 27.4 and 30.6±0.2, or ±0.1 such as about ±0.05 degrees.

11. The polymorph of claim 10, wherein the polymorph is characterised by a powder X-ray diffraction pattern comprising peaks expressed in degrees 2-theta at each of about 7.4, 9.3, 22.1, 22.5 and 23.6±0.2, or ±0.1 such as about ±0.05 degrees.

12. Form IV polymorph of ferric maltol characterized by a powder X-ray diffraction pattern comprising peaks expressed in degrees 2-theta at 9.5 and 14.5±0.2 degrees, and one or more further peaks expressed in degrees 2-theta selected from about 11.4, 12.8, 13.7, 15.5, 18.5, 19.9, 23.1, 25.0 and 25.8±0.2, or ±0.1 such as about ±0.05 degrees.

13. The polymorph of claim 12, wherein the polymorph is characterized by a powder X-ray diffraction pattern comprising peaks expressed in degrees 2-theta at each of 9.5, 11.4, 12.8, 14.5 and 15.5.

14. A polymorph obtainable by a process according to claim 4.

15. A composition comprising a mixture of Form I and Form II polymorphs.

16. A pharmaceutical composition comprising a polymorph as defined in claim 1, or a mixture thereof, and a pharmaceutically acceptable adjuvant, diluent or carrier.

17. A method for the treatment of iron deficiency with or without anaemia, such as iron deficiency anaemia, which method comprises the administration of a polymorph as defined in claim 1 to a subject in need of such treatment.

18. A polymorph obtainable by a process according to claim 9.

19. The polymorph of claim 5, wherein the polymorph comprises at least about 92 wt % ferric maltol based on the weight of the polymorph.

20. The polymorph of claim 8, wherein the polymorph further comprises one, two, three or more or each of 13.7, 19.6, 20.7, 22.5, 25.2 and 25.8±0.2, or ±0.1, such as about ±0.05 degrees.

21. The polymorph of claim 11, wherein the polymorph further comprises one, two, three or more, or each of, 11.6, 13.6, 14.0, 15.1, 17.0, 18.2, 24.9, or 27.4±0.2, or ±0.1 such as about ±0.05 degrees.

22. The polymorph of claim 13, wherein the polymorph further comprises one, two, three or more or each of 13.7, 18.5, 19.9, 23.1, 25.0 and 25.8 degrees±0.2, or ±0.1 such as about ±0.05 degrees.

23. A pharmaceutical composition comprising a polymorph as defined in claim 5, or a mixture thereof, and a pharmaceutically acceptable adjuvant, diluent or carrier.

24. A method for the treatment of iron deficiency with or without anaemia, such as iron deficiency anaemia, which method comprises the administration of a polymorph as defined in claim 5 to a subject in need of such treatment.

25. A pharmaceutical composition comprising a polymorph as defined in claim 10, or a mixture thereof, and a pharmaceutically acceptable adjuvant, diluent or carrier.

26. A method for the treatment of iron deficiency with or without anaemia, such as iron deficiency anaemia, which method comprises the administration of a polymorph as defined in claim 10 to a subject in need of such treatment.

27. A pharmaceutical composition comprising a polymorph as defined in claim 12, or a mixture thereof, and a pharmaceutically acceptable adjuvant, diluent or carrier.

28. A method for the treatment of iron deficiency with or without anaemia, such as iron deficiency anaemia, which method comprises the administration of a polymorph as defined in claim 12 to a subject in need of such treatment.

* * * * *